US011583426B2

(12) United States Patent
Cherian et al.

(10) Patent No.: US 11,583,426 B2
(45) Date of Patent: Feb. 21, 2023

(54) VESSEL LINING DEVICE AND RELATED METHODS

(71) Applicant: Teleflex Life Sciences Limited, Valletta (MT)

(72) Inventors: Shawn Sabu Cherian, Plymouth Meeting, PA (US); Francois Jouin, Malvern, PA (US); Greg A. Walters, Exton, PA (US)

(73) Assignee: Teleflex Life Sciences Limited, Valletta (MT)

( * ) Notice: Subject to any disclaimer, the term of this patent is extended or adjusted under 35 U.S.C. 154(b) by 106 days.

(21) Appl. No.: 16/807,781

(22) Filed: Mar. 3, 2020

(65) Prior Publication Data

US 2021/0275333 A1 Sep. 9, 2021

(51) Int. Cl.
*A61F 2/966* (2013.01)
*A61F 2/90* (2013.01)

(52) U.S. Cl.
CPC ............... *A61F 2/966* (2013.01); *A61F 2/90* (2013.01); *A61F 2002/9665* (2013.01)

(58) Field of Classification Search
CPC .... A61F 2/966; A61F 2/90; A61F 2002/9665; A61F 2/962; A61F 2/95; A61F 2002/9505; A61M 2025/0687; A61M 2025/0024; A61M 25/0662
See application file for complete search history.

(56) References Cited

U.S. PATENT DOCUMENTS

| 9,370,438 B2 | 6/2016 | Ginn |
| 9,545,298 B2 | 1/2017 | Ginn et al. |
| 10,729,544 B2 | 8/2020 | Ginn et al. |
| 2004/0098079 A1* | 5/2004 | Hartley ............ A61F 2/95 623/1.11 |
| 2005/0245958 A1 | 11/2005 | Carlson et al. |
| 2010/0174290 A1* | 7/2010 | Wuebbeling ...... A61F 2/95 606/108 |
| 2011/0282156 A1 | 11/2011 | Lenker et al. |
| 2012/0035548 A1 | 2/2012 | MacKenzie et al. |

(Continued)

OTHER PUBLICATIONS

PCT International Search Report dated Aug. 10, 2021 in PCT application No. PCT/US2021/019761.

(Continued)

*Primary Examiner* — Kelly J Bekker
*Assistant Examiner* — Andrew P. Restaino
(74) *Attorney, Agent, or Firm* — Gregory A. Grissett; Joseph P. Mathew

(57) ABSTRACT

A deployment device for lining a vessel having a housing having a proximal end and a distal end opposite the proximal end, the housing defining a guidewire channel, a tube elongated along a longitudinal axis, the tube having a proximal end and a distal end spaced from the proximal end of the tube along the longitudinal axis, a sheath assembly having a hub removably coupled to the distal end of the housing, and a mesh removably coupled to the tube and positioned along the tube. The tube and the sheath assembly are configured to move along the guidewire and into the vessel through a puncture and release the mesh inside the vessel when at least one of the tube and the mesh is actuated. The device is used as a method of mitigating potential injury or harm to the integrity of the patient's vessel lining.

29 Claims, 16 Drawing Sheets

(56) References Cited

U.S. PATENT DOCUMENTS

| | | | |
|---|---|---|---|
| 2013/0138201 | A1 | 5/2013 | Ginn |
| 2015/0094795 | A1 | 4/2015 | Ginn et al. |
| 2015/0165158 | A1 | 6/2015 | Ren et al. |
| 2018/0280173 | A1* | 10/2018 | Jimenez, Jr. ............ A61F 2/966 |
| 2019/0183525 | A9 | 6/2019 | Ginn et al. |
| 2019/0298557 | A1* | 10/2019 | Murray, III ........... A61F 2/2436 |
| 2020/0054861 | A1* | 2/2020 | Korkuch ........... A61M 25/0012 |
| 2020/0360140 | A1 | 11/2020 | Ginn et al. |
| 2020/0360165 | A1 | 11/2020 | Ginn et al. |
| 2020/0367929 | A1 | 11/2020 | Ginn et al. |

OTHER PUBLICATIONS

PCT Written Opinion dated Aug. 10, 2021 in PCT application No. PCT/US2021/019761.

\* cited by examiner

VESSEL LINING DEVICE AND RELATED METHODS

TECHNICAL FIELD

The present disclosure relates to devices and methods for lining a vessel.

BACKGROUND

Percutaneous procedures often involve accessing vasculature with elongated instruments, e.g., catheters, deployed in an ordered sequence. Common vasculature access points for such procedures include the femoral artery in a patient's groin area and the radial artery in the patient's forearm, each of which provides direct access to the central vasculature system, including the central venous system. For vascular procedures entry into the femoral arteries involves using a hollow needle to poke through a patient's skin, subcutaneous tissue and targeted vessel wall, thereby creating a puncture hole through each layer. After the needle poke, a guidewire is inserted through the needle until a distal end of the guidewire passes through the puncture hole and protrudes into the vessel lumen. From this puncture, all interventional equipment is then advanced into the artery to complete the operation.

As a result of these procedures, the inner lining of the vessel wall is exposed to various surgical equipment within the vessel. The vessel wall is therefore at risk to be damaged from the placement and advancement of these instruments. Potential complications can range from micro-scratching/tearing of the vessel walls to the unintentional dislodging of calcium or clots. These issues can lead to further complications during or after the surgical procedure.

SUMMARY

There is a need to provide better protection inside a vessel during surgical procedures in the vessel. An embodiment of the present disclosure is a deployment device configured to line a vessel. The deployment device includes a housing having a proximal end and a distal end opposite the proximal end, the housing defining a guidewire channel that extends from the distal end of the housing toward the proximal end. The deployment device further includes a tube elongated along a longitudinal axis. The tube has a proximal end and a distal end spaced from the proximal end of the tube along the longitudinal axis. The deployment device further includes a sheath assembly having a hub removably coupled to the distal end of the housing such that the housing is removable from the sheath assembly; and a mesh removably coupled to the tube and being positioned along the tube. At least one of the tube and the mesh are movable along the longitudinal axis in order to de-couple the mesh from the tube.

Another embodiment of the present disclosure is a method of lining a vessel. The method includes inserting a guidewire into the vessel through a puncture in the vessel. The method further includes sliding a deployment device along the guidewire and into the vessel until a distal end of the deployment device is inside the vessel. The method further includes actuating at least one of a tube and a mesh positioned along the tube to cause a lock to release the mesh from the distal end of the deployment device such that the mesh expands inside the vessel. The method further includes removing the tube from within the mesh in the vessel while maintaining the mesh in the vessel.

A further embodiment of the present disclosure is a deployment device configured to line a vessel. The deployment device includes a housing having a proximal end a distal end opposite the proximal end, and a guidewire channel that extends from the proximal end to the distal end of the housing. The deployment device further includes a tube extending relative to the housing in a distal direction. The deployment device further includes a sheath assembly having a hub removably coupled to the distal end of the housing, and a mesh removably coupled to the tube. The mesh is positioned along the tube in a compressed state. The deployment device further includes a lock that removably couples the mesh to the tube. The lock is configured to release the mesh from the tube.

A further embodiment of the present disclosure is a deployment device configured to line a vessel. The deployment device includes a housing having a proximal end, a distal end opposite the proximal end, and a guidewire channel that extends from the proximal end to the distal end of the housing. The deployment device further includes an inner tube extending relative to the housing in a distal direction. The deployment device further includes an outer tube extending relative to the housing in a distal direction and configured to surround the inner tube. The deployment device further includes a sheath assembly. The sheath assembly includes a hub removably coupled to the distal end of the housing. The sheath assembly further includes a mesh removably coupled to the outer tube, the mesh being positioned along the outer tube in a compressed state and configured to release from the outer tube when moved. The deployment device further includes a lock that removably couples the mesh to the outer tube and is configured to transition from a locked position to an unlocked position.

BRIEF DESCRIPTION OF THE DRAWINGS

The foregoing summary, as well as the following detailed description, will be better understood when read in conjunction with the appended drawings. The drawings show illustrative embodiments of the disclosure. It should be understood, however, that the application is not limited to the precise arrangements and instrumentalities shown.

DETAILED DESCRIPTION OF ILLUSTRATIVE EMBODIMENTS

Figure 1:
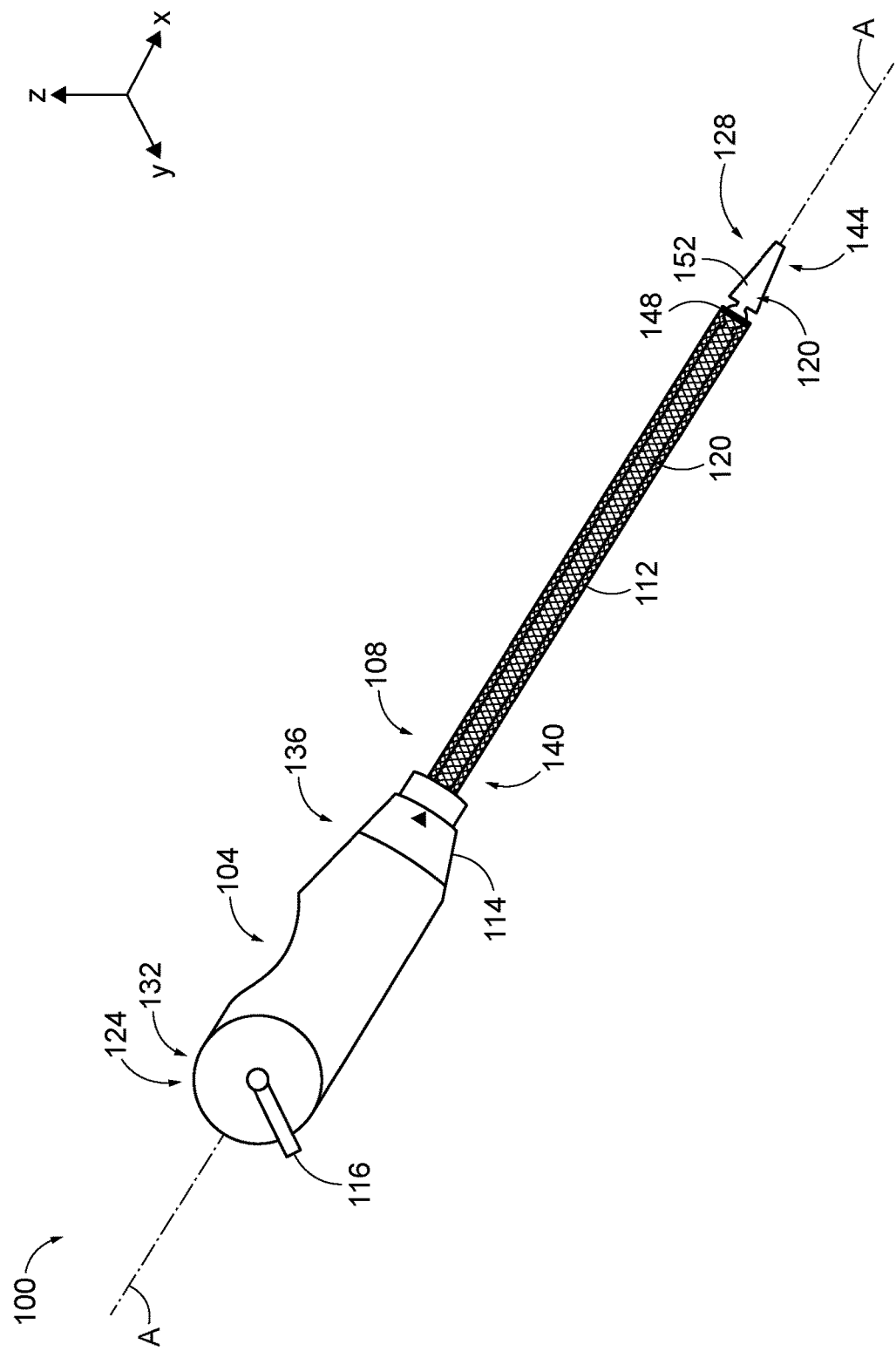
FIG. 1 is a perspective view of a deployment device according to an embodiment of the present disclosure.
Figure 3:
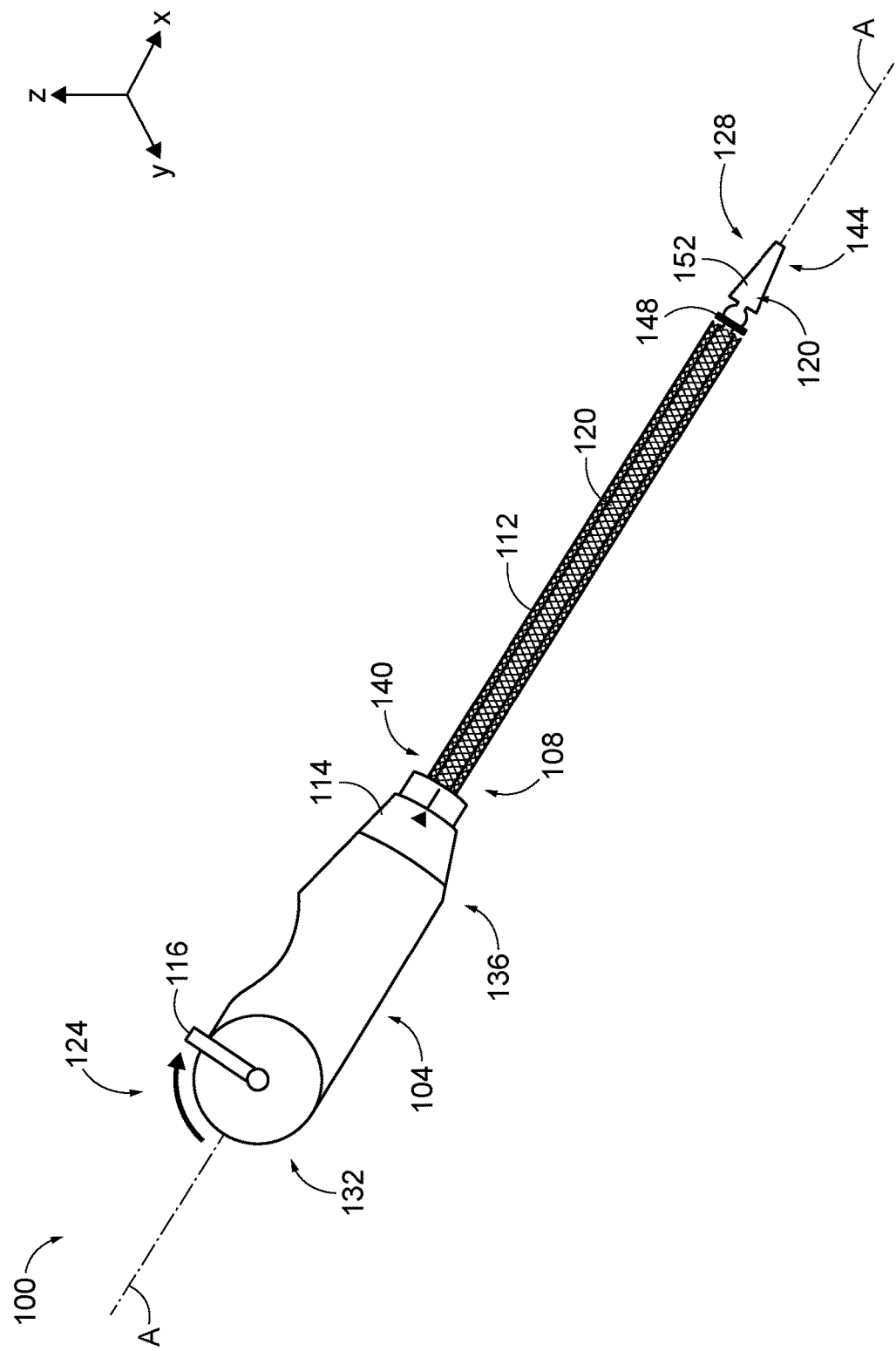
FIG. 3 is a perspective view of the deployment device shown in FIG. 1 in an unlocked position.

As shown in FIGS. 1 and 3, embodiments of the present disclosure include a deployment device 100 configured for use inside a vessel. The deployment device 100 is used to line an interior of a vessel in a patient's body during a surgical procedure performed by a user. The deployment device 100 may be actuated by the user in various ways to line the interior of the vessel, as further explained below.

Referring to FIGS. 1 and 3, an exemplary deployment device includes a housing assembly 104, a sheath assembly 108 having a mesh 112, an actuator 116 and a tube 120 coupled to the housing assembly 104. The deployment device extends along a central axis A and has a first end 124, where the housing assembly 104 is positioned, and a second end 128 opposite the first end 124 along the central axis A, where the tube 120 and sheath assembly 108 are positioned.

The housing assembly 104 is configured to allow a user to manipulate the deployment device 100 with the user's hands and insert the deployment device 100 into a patient's vessel via a puncture site. The housing assembly 104 has a proximal end 132 and a distal end 136 opposite the proximal end 132. The interior of the housing assembly 104 is sized to permit a guidewire (not depicted) to pass therethrough to insert the deployment device 100 into the vessel. The housing assembly 104 is operably coupled to the tube 120 at the distal end 136. In addition, the housing assembly 104 is removably coupled to the sheath assembly 108 at the distal end 136.

The sheath assembly 108 includes the mesh 112 and a hub 114 removably coupled to the distal end 136 of the housing assembly 104. In the illustrated embodiment, the mesh 112 is positioned along the tube 120. The mesh 112 is configured to be compressed against the tube 120 when the deployment device 100 is inserted into the vessel, and expand inside the vessel when released or decoupled from the tube 120. The mesh thus lines the interior of the vessel when it is released. In its compressed state, the mesh 112 surrounds the tube 120 and is removably coupled to the hub 114 and to the tube 120. In the illustrated embodiment, the inner diameter of the mesh 112 when compressed against the tube 120 is 7 French ("FR"), or approximately 1 mm. In other embodiments, the inner diameter of the mesh 112 may vary. In the illustrated embodiment, the inner diameter of the mesh 112 when expanded is sized to conform or contact the vessel. In alternative embodiments, the inner diameter of the mesh 112 when expanded may vary. The mesh 112 must be comprised of a flexible material in order to be compressed around the tube 120 and also expand to line the interior of the vessel. However, the mesh 112 must also be strong enough to protect the interior vessel from the insertion and removal of various equipment. In the illustrated embodiment, the mesh 112 is made of nitinol. In alternative embodiments, the mesh 112 may be made of various materials, including stainless steel, other metallic alloys, nylon, polyurethane, or other polymers.

The actuator 116 is configured to extend the tube 120 in a distal direction from a first position to a second position that is distal to the first position along the central axis A when the actuator 116 is engaged, thereby releasing the mesh 112 from the tube 120 and into the vessel. The actuator 116 is coupled to the proximal end 132 of the housing assembly 104. The actuator 116 is also operably coupled to the tube 120. In the illustrated embodiment, the actuator is a release lever; however, in alternative embodiments, the type of actuator may vary. The release lever rotates about the y-axis, which causes a transfer of rotational motion of the lever to translational motion of the tube 120 in the distal direction about the perpendicular x-axis. The tube 120 extends in a distal direction along the central axis A. The movement of the tube 120 releases the compressed mesh 112.

The tube 120 is configured to be inserted inside the vessel via the puncture site and is further configured to transport the mesh 112 inside the vessel. The tube 120 is sized to permit a guidewire (not depicted) to pass therethrough. The tube 120 is elongated along the central axis A and has a proximal end 140 and a distal end 144. The tube 120 has a length that extends from the proximal end 140 to the distal end 144 along the central axis A. In the illustrated embodiment, the length of the tube can vary as clinically required. In alternative embodiments, the length of the tube 120 may vary. The proximal end 140 of the tube 120 is coupled to the distal end 136 of the housing assembly 104.

Figure 2:
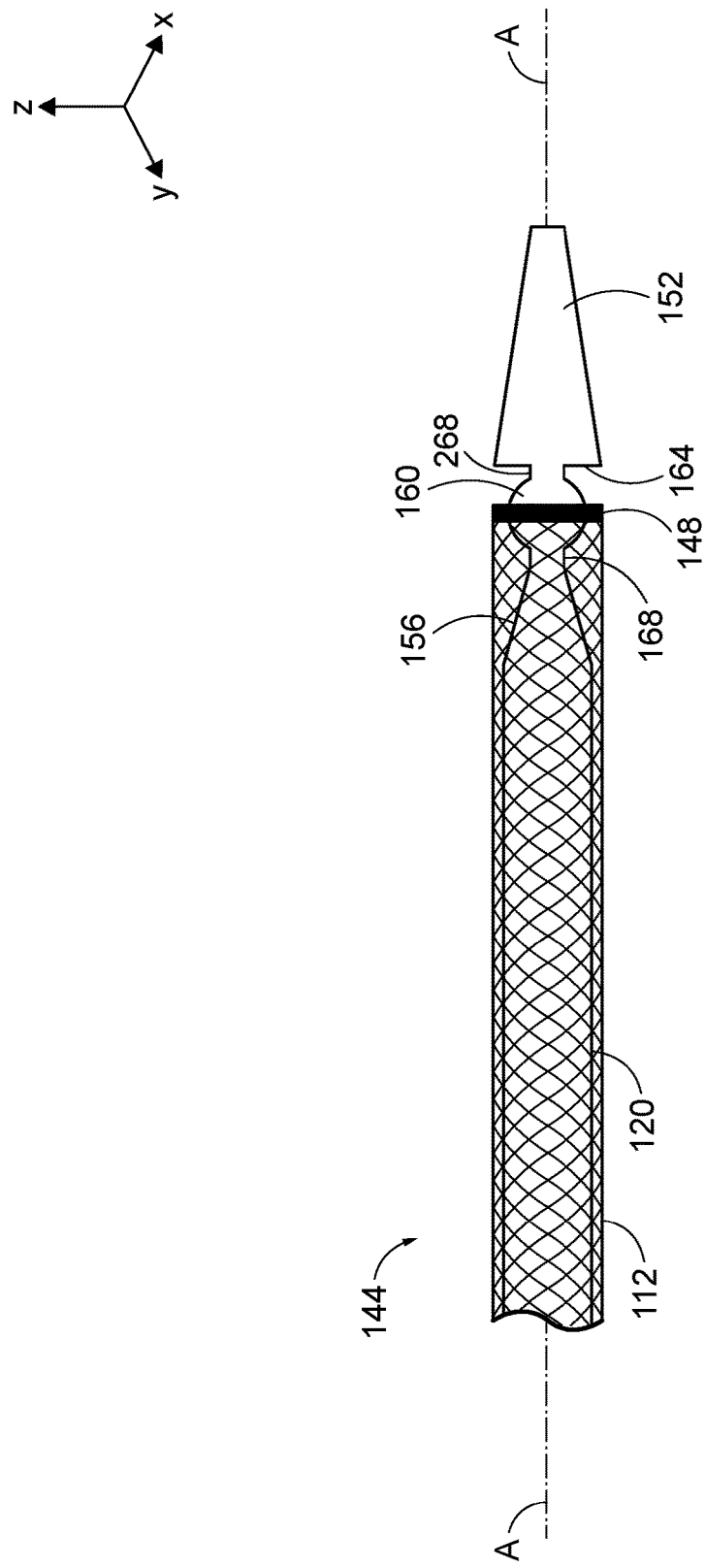
FIG. 2 is a side view of a distal end of a tube of the deployment device shown in FIG. 1.
Figure 4:
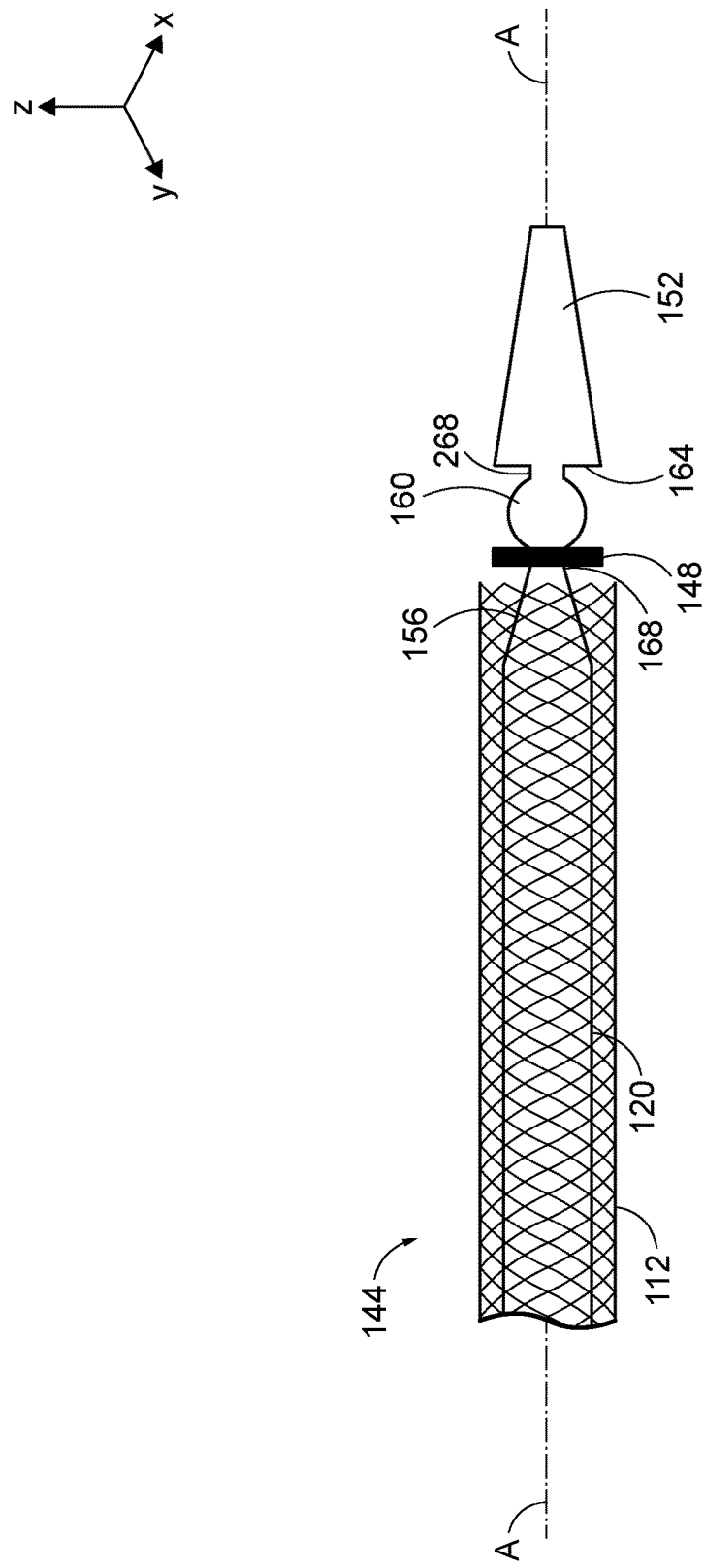
FIG. 4 is a side view of a distal end of a tube of the deployment device shown in FIG. 3.

Referring to FIGS. 2 and 4, the distal end 144 of the tube 120 includes a lock 148 and a tip 152. In the illustrated embodiment, the lock 148 is configured to transition between a locked position and an unlocked position when the tube 120 is actuated by the actuator 116. In the illustrated embodiment, the mesh 112 is fixed to the tube 120 in the locked position, and the mesh 112 is not fixed to the tube 120 in the unlocked position. The lock 148 is configured to hold the mesh 112 in a compressed state against the distal end of the tube 120 when the lock 148 is in the locked position. The lock 148 is further configured to release the mesh from the distal end of the tube when the lock is in the unlocked position. In the illustrated embodiment, the lock 148 is a metallic ring. In alternative embodiments, the shape and composition of the lock 148 may vary.

The lock 148 is positioned on a portion of the tip 152. The tip 152 is sized and shaped to be inserted smoothly into the vessel and allow the lock 148 to transition from a locked position to an unlocked position. In the illustrated embodiment, a distal portion of the tip 152 is conical in shape. In another embodiment, the distal portion of the tip 152 may be round in shape. In alternative embodiments, the shape of the tip 152 may vary. In the present disclosure, the tip 152 includes a proximal surface 156, a protrusion 160 located in a distal direction along the central axis A from the proximal surface 156, and a distal stop surface 164 located in a distal direction along the central axis A from the proximal surface 156 and the protrusion 160. The protrusion 160 is therefore positioned between and spaced from the proximal surface 156 and the distal stop surface 164. The proximal surface 156 and protrusion 160 are separated by a proximal groove 168. Similarly, the distal stop surface 164 and the protrusion 160 are separated by a distal groove 268.

The lock is disposed between the proximal surface 156 and the distal stop surface 164. The distal stop surface 164 is sized to prevent the lock 148 from advancing over the tip 152. In the present disclosure, the diameter of the distal stop surface 164 is larger than the diameter of the lock 148 to stop the lock 148 from moving past the distal stop surface 164 in the distal direction. The proximal surface 156 tapers in a distal direction toward the proximal groove 168 and the protrusion 160 to aid in insertion of the tip into the patient's vessel.

The lock 148 is positioned on the protrusion 160 and compresses the mesh 112 against the protrusion 160 in the locked position. The lock 148 is released from the protrusion 160 and moves in the proximal direction toward the proximal surface 156 in the unlocked position. The diameter of the tube 120 is sized to stop the lock 148 from advancing past the proximal surface 156 in the proximal direction, and the lock 148 is displaced into the proximal groove 168. Upon release of the lock 148 from the protrusion 160, the lock 148 releases the mesh 112 from the tube 120. The lock 148 transitions from the locked position to the unlocked position when the actuator 116 (not depicted) actuates the tube 120 to extend in a distal direction along the central axis A.

FIGS. 1 and 2 illustrate the deployment device 100 prior to engagement of the actuator 116. Prior to engagement of the actuator 116, the lock 148 is in the locked position. The mesh 112 surrounds the tube and is compressed between the lock 148 and the protrusion 160 at the distal end 144 of the tube 120. This configuration allows the deployment device 100 to be compact in order to be inserted into the patient's vessel. FIGS. 3 and 4 illustrate the deployment device shown in FIGS. 1-2, upon engagement of the actuator 116. In the illustrated embodiment, rotation of the actuator 116 about the y-axis causes translational motion of the tube 120 in the distal direction about the x-axis. Rotation of the actuator 116 causes the tube 120 to extend in a distal direction along the central axis A. Extension of the tube 120 transitions the lock 148 from the locked position on the protrusion 160 to the unlocked position on the proximal groove 168, thereby releasing the compressed mesh 112 from the tube 120. The mesh 112 then expands in the vessel to line the interior of the vessel.

Figure 5:
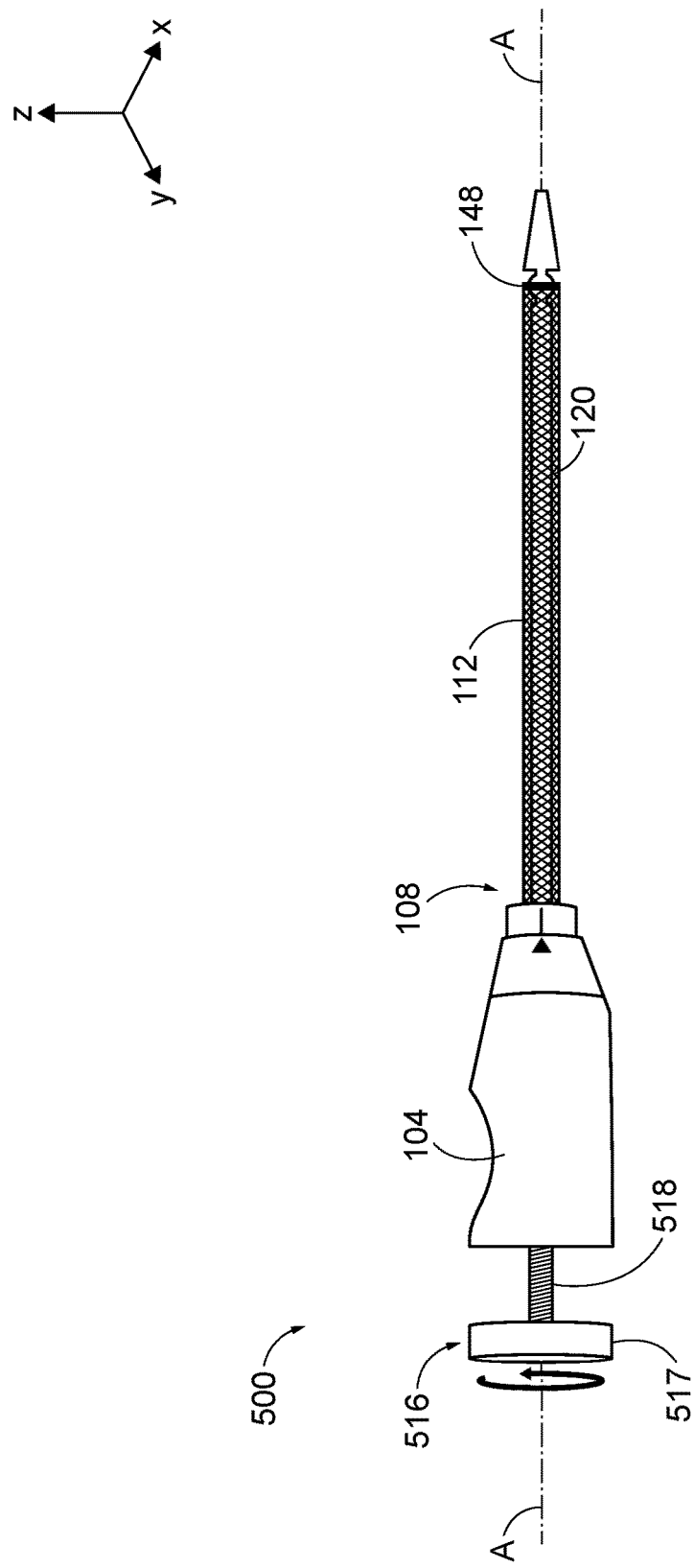
FIG. 5 is a perspective view of a deployment device according to another embodiment of the present disclosure.

FIG. 5 is a perspective view of a deployment device 500 according to another embodiment of the present disclosure. The deployment device 500 includes the same housing assembly 104, tube 120, and sheath assembly 108 of the deployment device 100 shown in FIGS. 1-4 and described above. Therefore, the features and functionalities disclosed above for the deployment device 100 apply to the deployment device 500 shown in FIG. 5 and will have the same reference numbers. Referring to FIG. 5, in the illustrated embodiment, the actuator 516 is a screw having a screw head 517 and a threaded body 518 that is configured to be rotated by a user about the x-axis. The screw 516 is positioned such that the screw head 517 is disposed on the outer surface of the housing assembly 104 and at least a portion of the threaded body 518 is disposed within the housing assembly 104. The threaded body 518 is operably coupled to the tube 120 inside the housing assembly 104.

When a user rotates the screw 516 about the x-axis via the screw head 517, the threaded body 518 of the screw 516 provides translational movement of the tube 120 about the same axis. Rotation of the screw 516 therefore extends the tube 120 in the distal direction along the central axis A. Extension of the tube 120 transitions the lock 148 from the locked position on the protrusion 160 to the unlocked position off of the protrusion 160 and in the proximal groove 168, thereby releasing the compressed mesh 112. The mesh 112 then expands in the patient's vessel to line the interior of the vessel.

Figure 6:
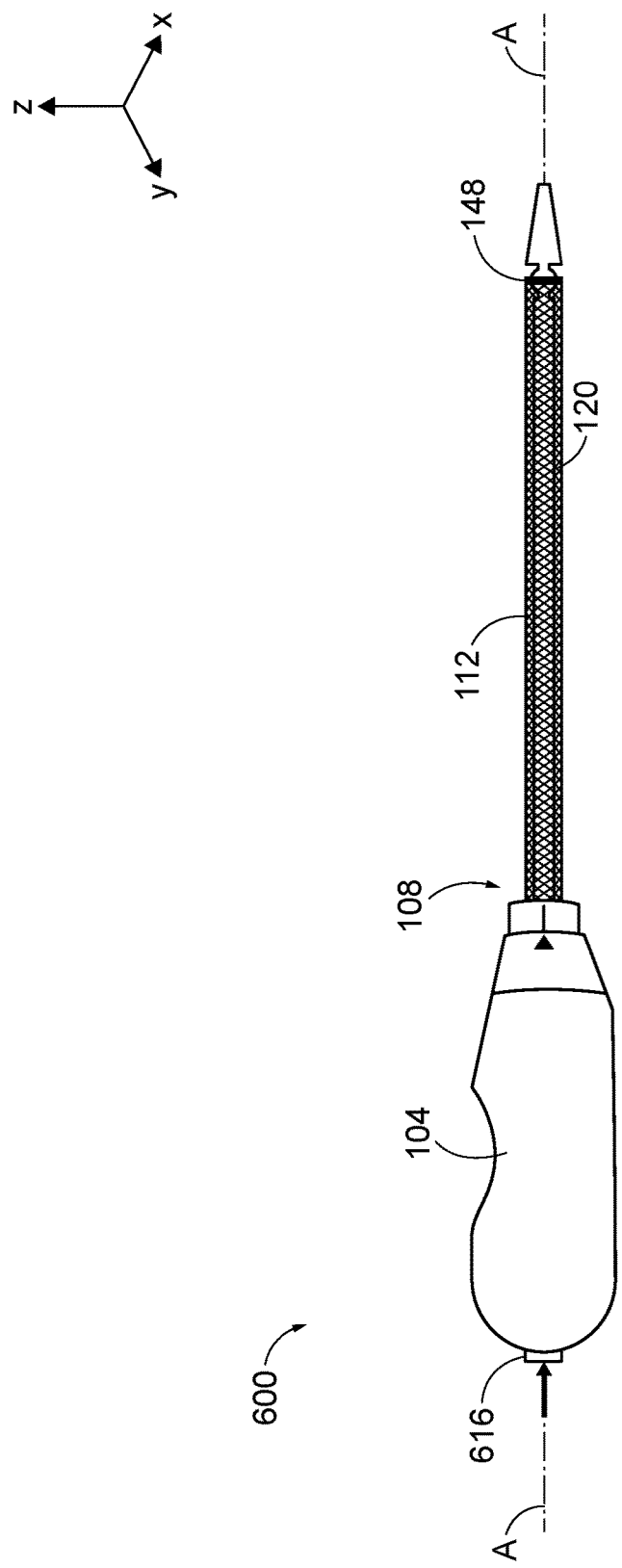
FIG. 6 is a perspective view of a deployment device according to another embodiment of the present disclosure.

FIG. 6 is a perspective view of a deployment device 600 according to another embodiment of the present disclosure. The deployment device 600 includes the same housing assembly 104, tube 120, and sheath assembly 108 of the deployment device 100 shown in FIGS. 1-4 and described above. Therefore, the features and functionalities disclosed above for the deployment device 100 apply to the deployment device 600 shown in FIG. 6 and will have the same reference numbers. Referring to FIG. 6, in the illustrated embodiment, the actuator 616 is a button coupled to a spring (not depicted) that is configured to be depressed by a user about the x-axis. The button 616 is disposed on the outer surface of the housing assembly 104 and the spring is disposed within the housing assembly 104. The spring is operably coupled to the tube 120 inside the housing assembly 104.

When a user depresses the button 616 about the x-axis, the spring transfers compressive energy from the depression of the button 616 into translational movement in the tube 120 about the same axis. Depression of the button 616 extends the tube 120 in the distal direction along the central axis A. Extension of the tube 120 transitions the lock 148 from the locked position on the protrusion 160 to the unlocked position off of the protrusion 160 and in the proximal groove 168, thereby releasing the compressed mesh 112. The mesh 112 then expands in the patient's vessel to line the interior of the vessel.

Figure 7:
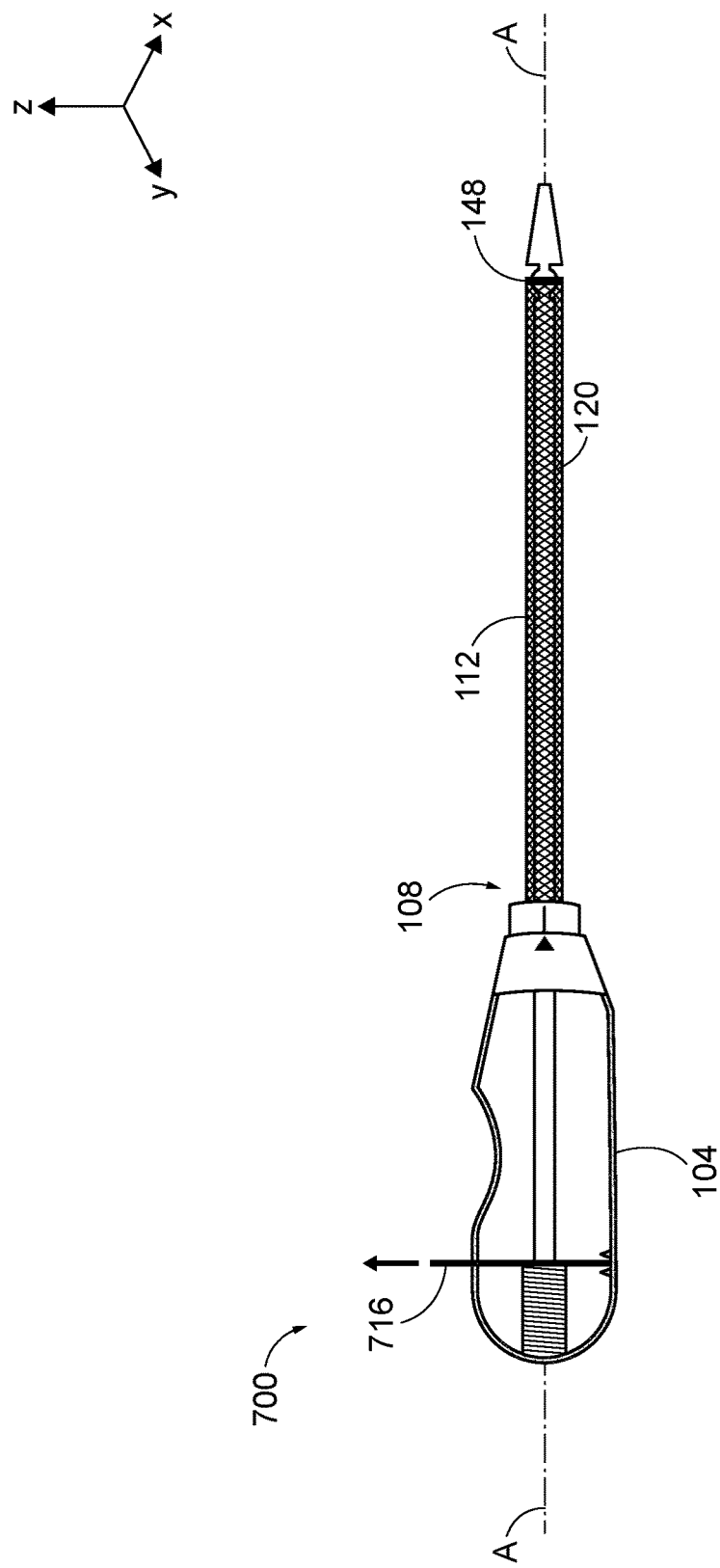
FIG. 7 is a perspective view of a deployment device according to another embodiment of the present disclosure.

FIG. 7 is a perspective view of a deployment device 700 according to another embodiment of the present disclosure. The deployment device 700 includes the same housing assembly 104, tube 120, and sheath assembly 108 of the deployment device 100 shown in FIGS. 1-4 and described above. Therefore, the features and functionalities disclosed above for the deployment device 100 apply to the deployment device 700 shown in FIG. 7 and will have the same reference numbers. Referring to FIG. 7, in the illustrated embodiment, the actuator 716 is a pin coupled to a spring (not depicted) that is configured to be displaced by a user about the z-axis. The pin 716 is disposed on the outer surface of the housing assembly 104 and the spring is disposed within the housing assembly 104. The spring is operably coupled to the tube 120 and is oriented about the x-axis.

Prior to displacement of the pin 716, the spring is in a compressed state. When a user displaces the pin 716 about the z-axis, the spring is released about the x-axis, providing translational movement of the tube 120 in the distal direction about the x-axis. Displacement of the pin 716 extends the tube 120 in the distal direction along the central axis A. Extension of the tube 120 transitions the lock 148 from the locked position on the protrusion 160 to the unlocked position off of the protrusion 160 and in the proximal groove 168, thereby releasing the compressed mesh 112. The mesh 112 then expands in the patient's vessel to line the interior of the vessel.

Figure 8:
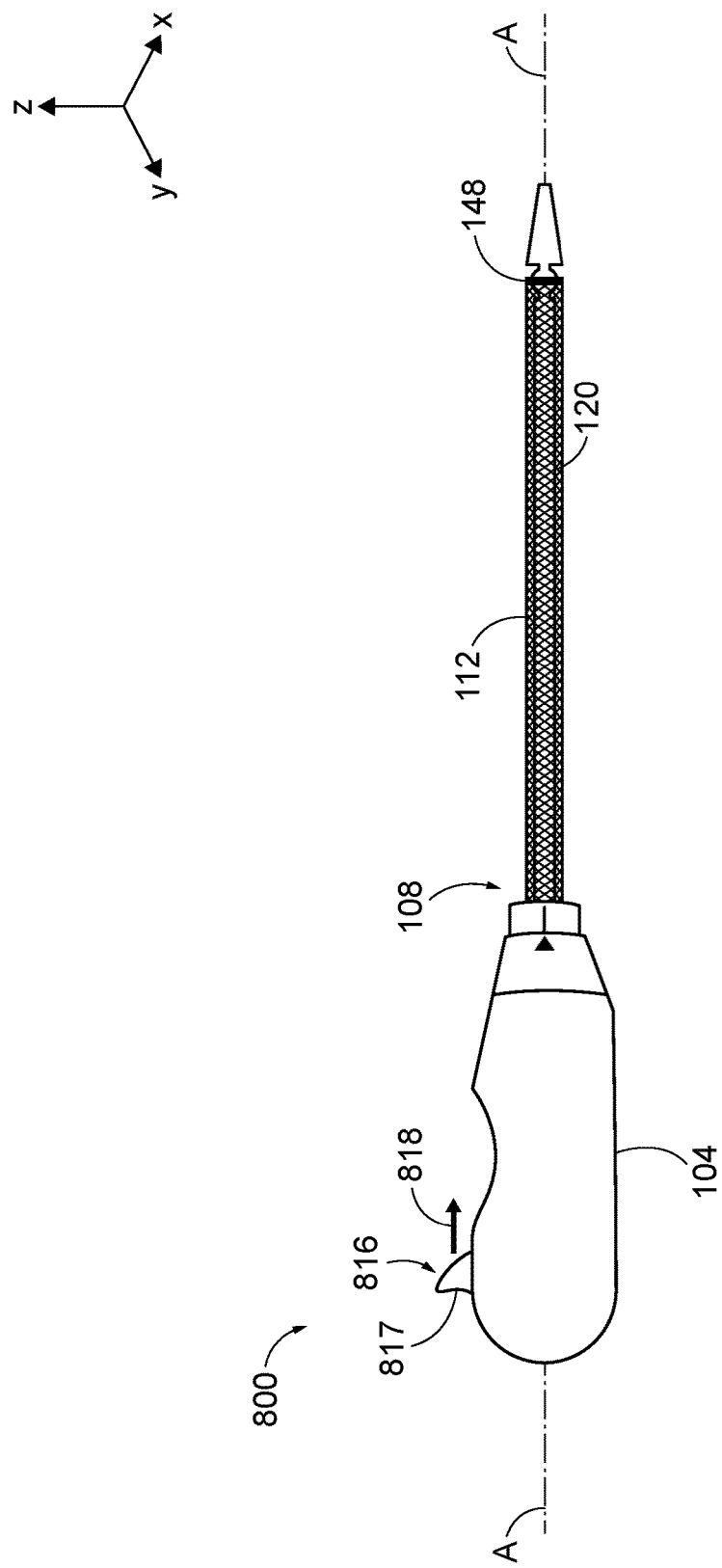
FIG. 8 is a perspective view of a deployment device according to another embodiment of the present disclosure.

FIG. 8 is a perspective view of a deployment device 800 according to another embodiment of the present disclosure. The deployment device 800 includes the same housing assembly 104, tube 120, and sheath assembly 108 of the deployment device 100 shown in FIGS. 1-4 and described above. Therefore, the features and functionalities disclosed above for the deployment device 100 apply to the deployment device 800 shown in FIG. 8 and will have the same reference numbers. Referring to FIG. 8, in the illustrated embodiment, the actuator 816 is a tab configured to be moved in a distal direction along a track 817 about the x-axis. The tab 816 and track 817 are disposed on the outer surface of the housing assembly 104 and are both coupled to the tube 120. The track 817 comprises at least one ridge along the track to prevent the tab 816 from progressing along the track 817 in a proximal direction.

When a user progresses the tab 816 along the track 817 about the x-axis, the tab 816 and track 817 provide translational movement of the tube 120 in the distal direction about the same axis. Extension of the tube 120 transitions the lock from the locked position on the protrusion 160 to the unlocked position off of the protrusion 160 and in the proximal groove 168, thus releasing the compressed mesh 112. The mesh 112 then expands in the patient's vessel to line the interior of the vessel. When the tab 816 is progressed over the at least one ridge, the tab 816 locks in the current position, preventing the tab 816 from progressing in the proximal direction and preventing translational movement of the tube 120 in a proximal direction about the x-axis.

Figure 9:
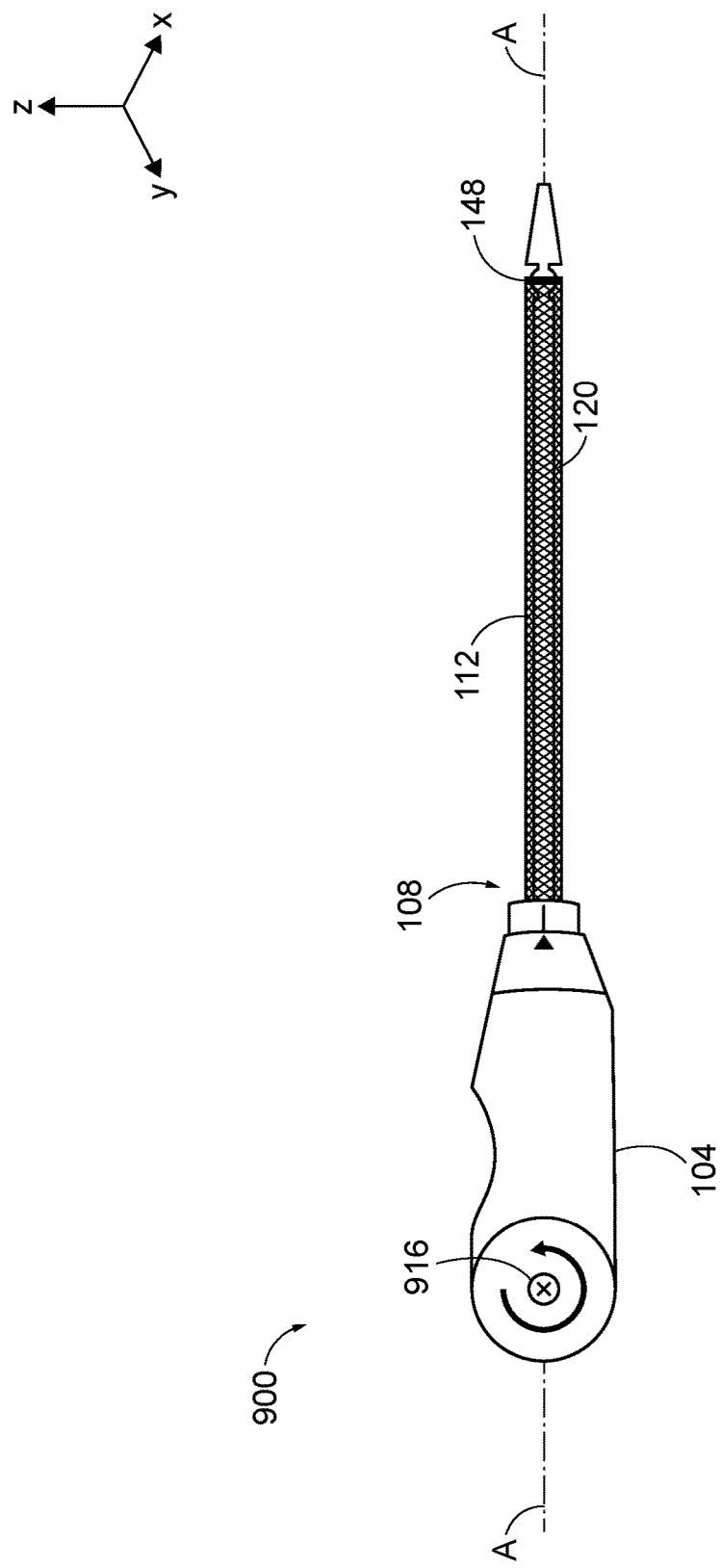
FIG. 9 is a perspective view of a deployment device according to another embodiment of the present disclosure.

FIG. 9 is a perspective view of a deployment device 900 according to another embodiment of the present disclosure. The deployment device 900 includes the same housing assembly 104, tube 120, and sheath assembly 108 of the deployment device 100 shown in FIGS. 1-4 and described above. Therefore, the features and functionalities disclosed above for the deployment device 100 apply to the deployment device 900 shown in FIG. 9 and will have the same reference numbers. Referring to FIG. 9, in the illustrated embodiment, the actuator 916 is a gear coupled to a track system (not depicted) that is configured to be rotated by a user about the y-axis. The gear 916 is disposed on the outer surface of the housing assembly 104 while the track system is disposed in the interior of the housing assembly 104. The track system is coupled to the tube 120.

When a user rotates the gear 916 about the y-axis, the track system provides translational movement of the tube 120 in the distal direction about the x-axis. The tube 120 extends in a distal direction along the central axis A, causing the lock 148 to transition from the locked position on the protrusion 160 to the unlocked position off of the protrusion 160 and in the proximal groove 168, thereby releasing the compressed mesh 112. The mesh 112 then expands in the patient's vessel to line the interior of the vessel.

Figure 10A:
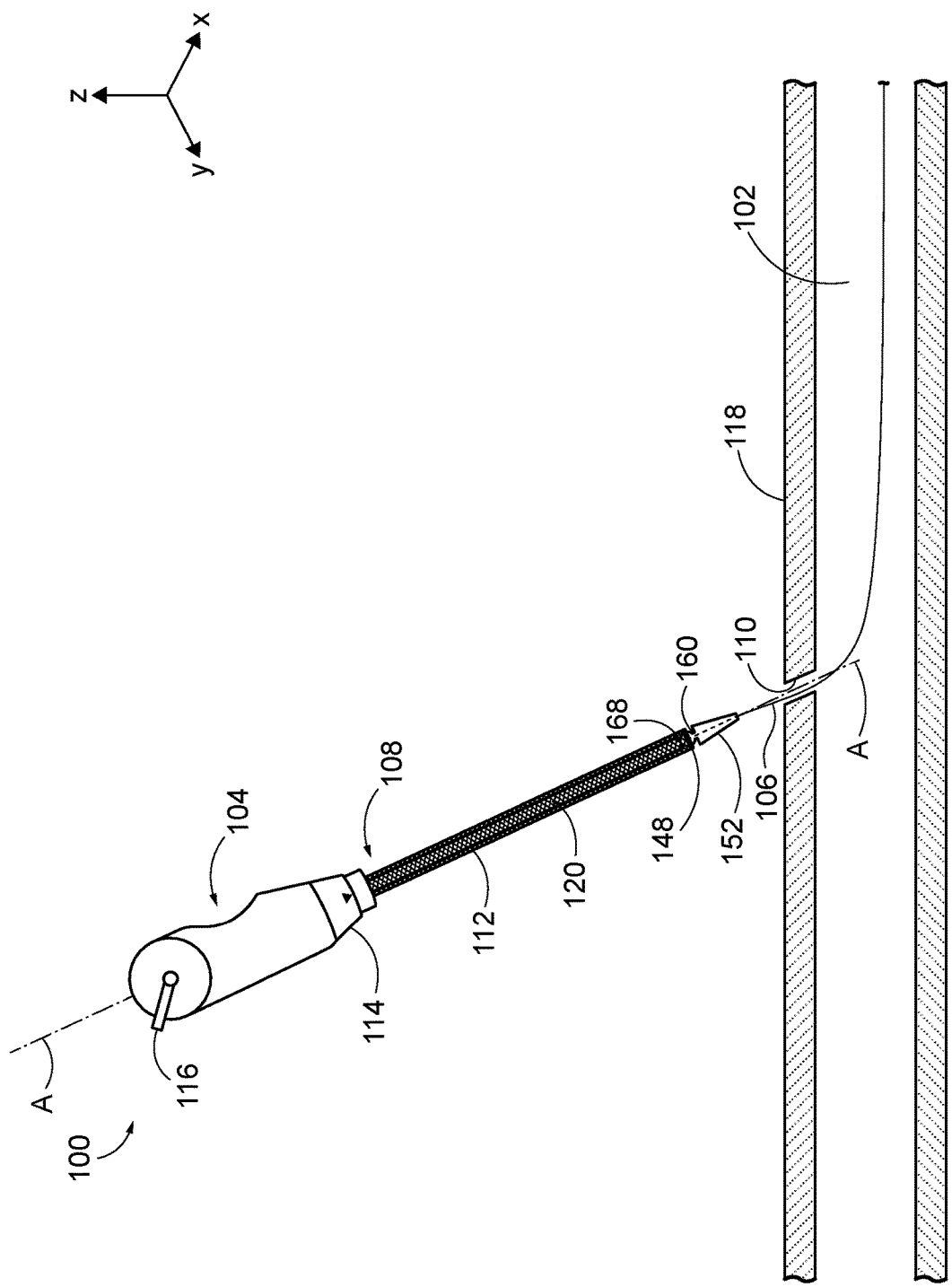
FIG. 10A is a schematic side view of a deployment device prior to implementation in a vessel, according to an embodiment of the present disclosure.

FIGS. 10A-10D illustrate the deployment device 100 shown in FIGS. 1-4, as the deployment device 100 is inserted and releases the mesh 112 in a vessel 102. Referring to FIG. 10A, a guidewire 106 is inserted into a puncture site 110 of the vessel 102. In the illustrative embodiment, the guidewire 106 is fed through the tip 152 of the deployment device. In alternative embodiments, the deployment device 100 may be placed onto the guidewire 106 by any means known in the art. At this stage, the actuator 116 is not engaged. The mesh 112 surrounds the tube 120 and is compressed against the protrusion 160 by the lock 148.

Figure 10B:
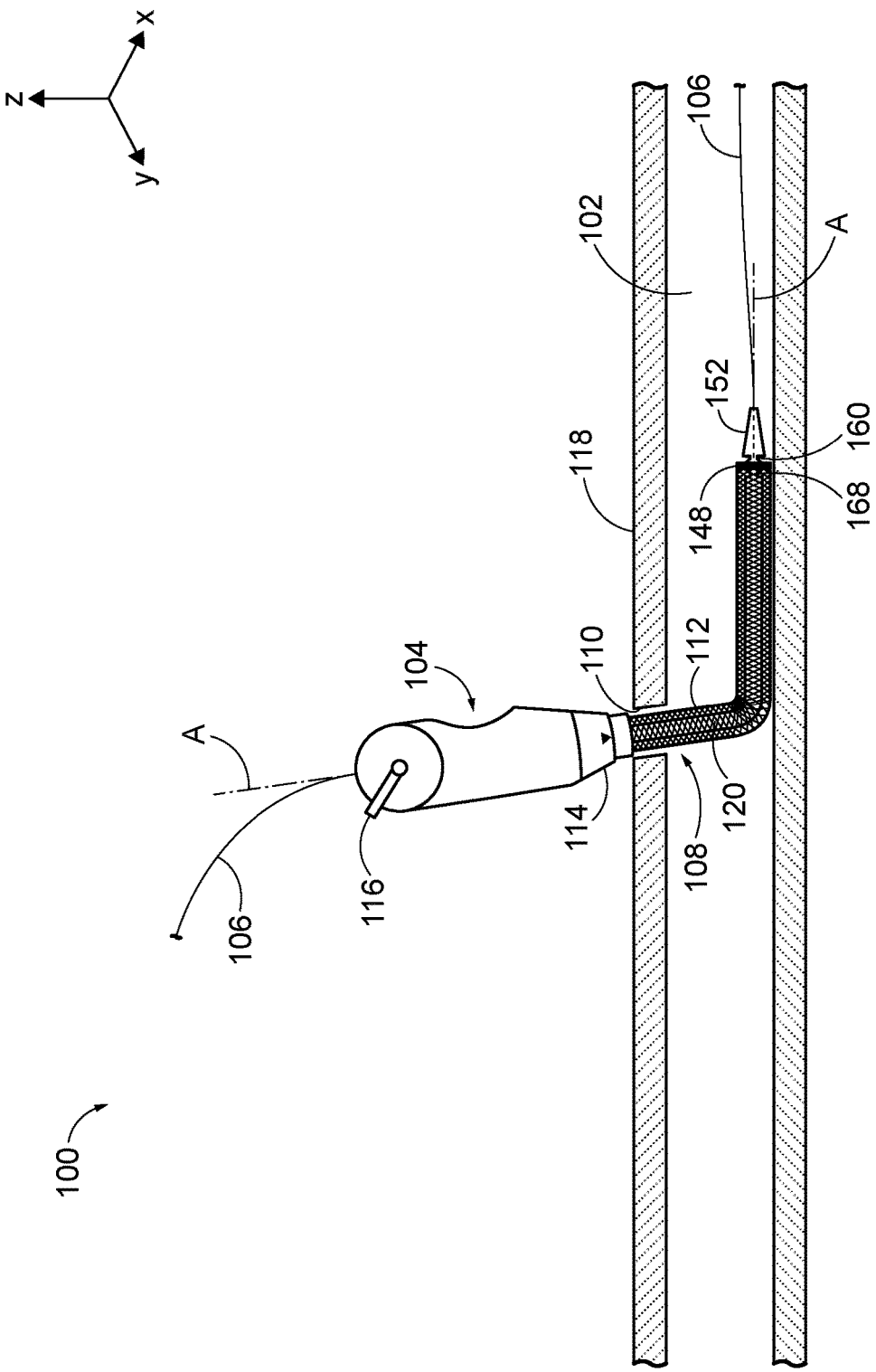
FIG. 10B is a schematic side view of the deployment device shown in FIG. 10A implemented in the vessel.

Referring to FIG. 10B, the deployment device 100 is inserted into the vessel 102 through the puncture site 110. At this stage, the actuator 116 is not engaged, and the mesh 112 remains compressed between the lock 148 and the protrusion 160. The deployment device 100 is progressed into the vessel 102 until the hub 114 contacts the patient's skin 118.

Figure 10C:
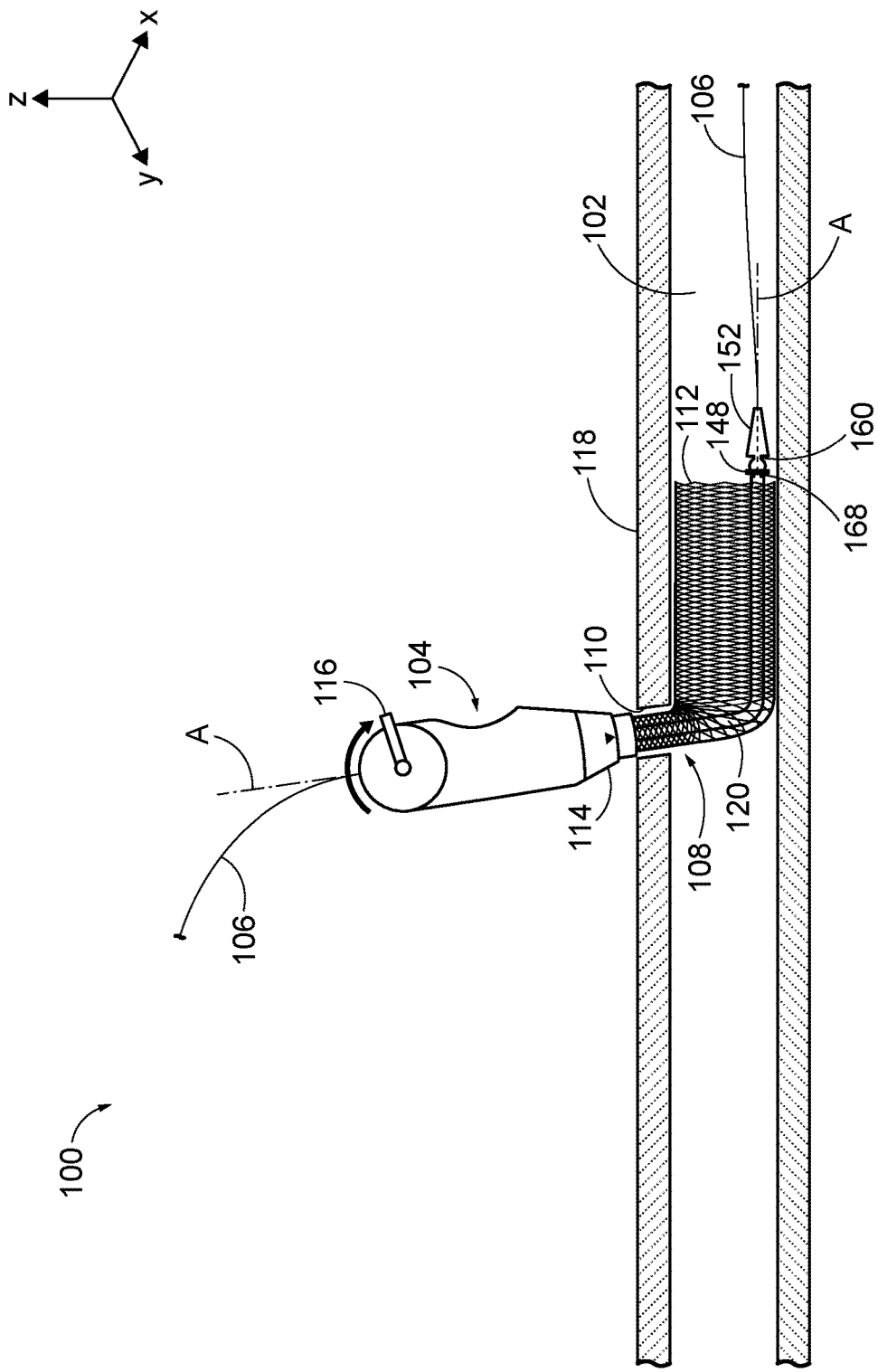
FIG. 10C is a schematic side view of the deployment device shown in FIGS. 10A and 10B deploying the mesh inside the vessel.

Referring to FIG. 10C, the actuator 116 can be engaged by the user once the hub 114 contacts the patient's skin 118. Engagement of the actuator 116 causes the tube 120 to extend in a distal direction along the central axis A past its original position. Extension of the tube 120 in the distal direction releases the lock 148 from its position on the protrusion 160 and causes the lock 148 to fall in the proximal groove 168. Movement of the lock 148 releases the mesh 112, which causes the mesh 112 to expand inside the vessel 102. The mesh 112 is configured to expand to line the interior of the vessel 102.

Figure 10D:
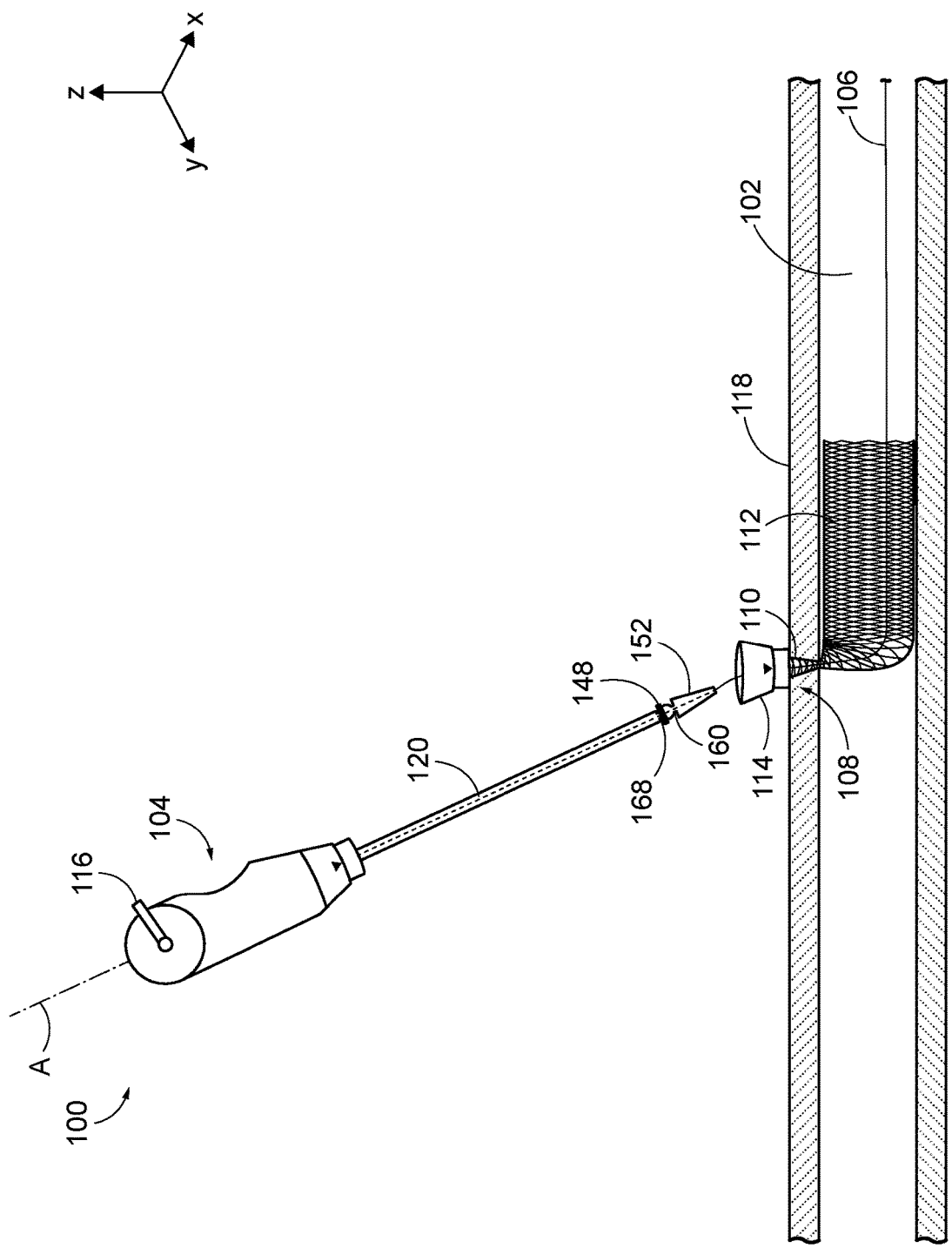
FIG. 10D is a schematic side view of the deployment device shown in FIGS. 10A, 10B, and 10C being removed from the vessel.

Referring to FIG. 10D, the deployment device 100 is uncoupled from the sheath assembly 108 and is removed from the vessel 102. The hub 114 remains in contact with the patient's skin 118 over the puncture site 110 and the mesh 112 remains inside the vessel so that the remainder of the procedure can be completed. The hub 114 and the mesh 112 may be subsequently removed upon completion of the procedure and the puncture site 110 may subsequently be sealed.

Figure 11:
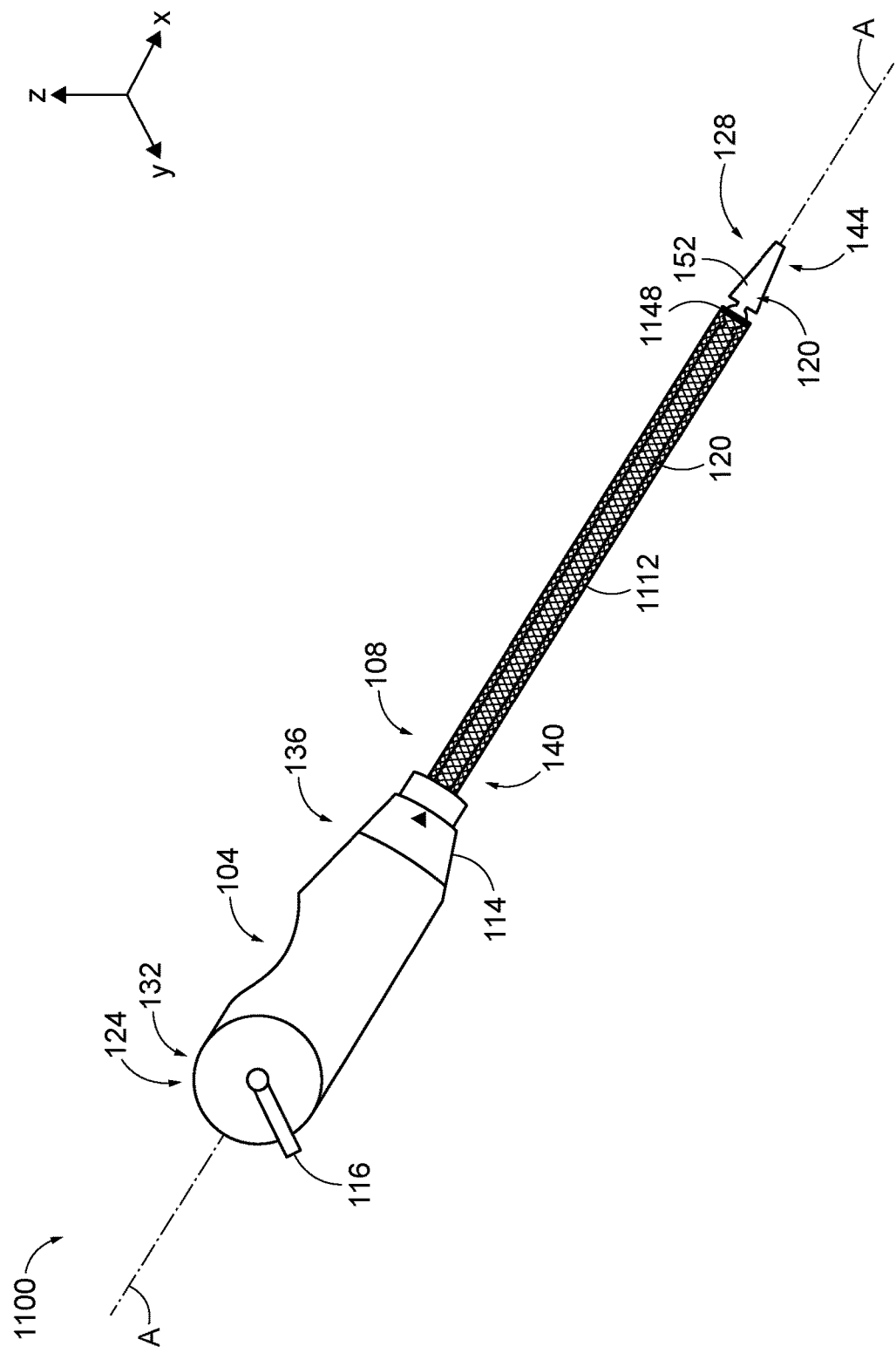
FIG. 11 is a perspective view of a deployment device 1100 according to another embodiment of the present disclosure.

FIG. 11 is a side view of a deployment device 1100 according to another embodiment of the present disclosure. The deployment device 1100 includes the same housing assembly 104, tube 120, actuator 116, and hub 114 of the deployment device 100 shown in FIGS. 1-4 and described above. Therefore, the features and functionalities disclosed above for the deployment device 100 apply to the deployment device 1100 shown in FIG. 11 and will have the same reference numbers. Referring to FIG. 11, the deployment device further includes a mesh 1112 and a lock 148. The mesh 1112 is configured to be compressed against the tube 120 when the deployment device 1100 is inserted into a patient's vessel, and expand inside the vessel when released from the tube 120. The mesh thus lines the interior of the vessel when it is released. In its compressed state, the mesh 1112 surrounds the tube 120 and is removably coupled to the hub 114 and to the tube 120. The mesh 1112 is operably coupled to the actuator 116.

The distal end 144 of the tube 120 includes the lock 1148. The lock 1148 is configured to hold the mesh 1112 in a compressed state against the tube 120 in a locked position prior to engagement of the actuator 116. The lock 1148 is disposed on a portion of the tip 152. The lock 1148 is positioned on the protrusion 160 and compresses the mesh 1112 against the protrusion 160 prior to engagement of the actuator 116. This configuration allows the deployment device 1100 to be compact in order to be inserted into the patient's vessel. Once the deployment device 1100 is inserted into the patient's vessel, the actuator 116 may be engaged.

In the illustrated embodiment, engagement of the actuator 116 about the x-axis causes translational motion of the mesh 1112 in the x-axis. For example, rotation of the actuator 116 causes the mesh 1112 to retract in a proximal direction along the central axis A. Retraction of the mesh 1112 releases the mesh 1112 from beneath the lock 1148. The mesh 1112 then expands in the vessel to line the interior of the vessel. In the illustrated embodiment, retraction of the mesh 1112 causes the lock 1148 to be transition from the locked position on the protrusion 160 to an unlocked position on the proximal groove 168. In alternative embodiments, the lock may stay in place on the protrusion 160 when the mesh 1112 retracts.

Figure 12:
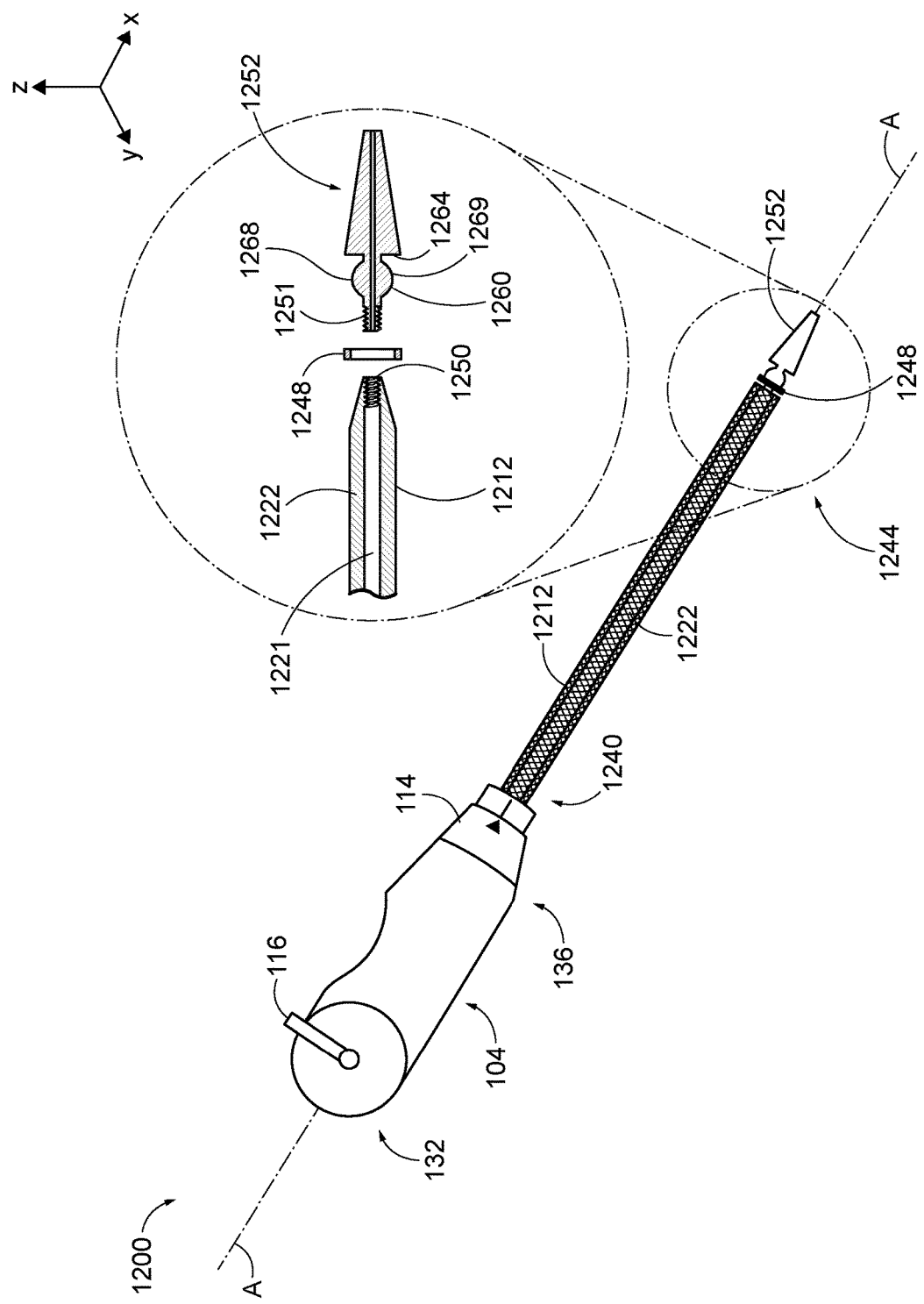
FIG. 12 is a perspective view of a deployment device 1100 according to another embodiment of the present disclosure.

FIG. 12 is a side view of a deployment device 1200 according to another embodiment of the present disclosure. The deployment device 1200 includes the same housing assembly 104, actuator 116, and hub 114 of the deployment device 100, 1100 shown in FIGS. 1-4, 11 and described above. Therefore, the deployment device 100, 1100 and the deployment device 1200 shown in FIG. 12 and will have the same reference numbers. Referring to FIG. 12, the deployment device further includes an inner tube 1221 and an outer tube 1222 that surrounds the inner tube 1221. The inner tube 1221 and the outer tube 1222 are hollow tubes and are concentric to each other.

The inner tube 1221 and the outer tube 1222 are configured to be inserted inside the vessel via the puncture site. The inner tube 1221 is sized to permit a guidewire (not depicted) to pass therethrough. The inner tube 1221 therefore has a diameter of approximately 6 FR, while the outer tube 1222 has a diameter of approximately 8 FR. The inner tube 1221 and outer tube 1222 are elongated along the central axis A and have a proximal end 1240 and a distal end 1244. The inner tube 1221 and the outer tube 1222 have a length that extends from the proximal end 1240 to the distal end 1244 along the central axis A. The proximal end 1240 is coupled to the distal end 136 of the housing assembly 104. The distal end 1244 tapers in a distal direction and includes a screw insert 1250.

The deployment device 1200 further includes a tip 1252. The tip 1252 is sized and shaped to be inserted smoothly into the vessel. In the illustrated embodiment, a distal portion of the tip 1252 is conical in shape. In another embodiment, the distal portion of the tip 1252 may be round in shape. In alternative embodiments, the shape of the tip 1252 may vary. In the present disclosure, the tip 1252 includes a screw head 1251 located in a proximal direction along the central axis A, a protrusion 1260 located in a distal direction along the central axis A from the screw head 1251, and a distal stop surface 1264 located in a distal direction along the central axis A from the screw head 1251 and the protrusion 1260. The protrusion 1260 is therefore positioned between and spaced from the screw head 1251 and the distal stop surface 1264. The screw head 1251 and protrusion 1260 are separated by a proximal groove 1268. Similarly, the distal stop surface 1264 and the protrusion 1260 are separated by a distal groove 1269.

The tip 1252 is configured to be attached to the inner tube 1221 and the outer tube 1222. Specifically, the screw head 1251 is configured to be inserted into the screw insert 1250. The tip 1252 includes a hollow channel that extends along the length of the tip 1252 to allow a guidewire to pass through both the tip 1252 and the inner tube 1221 when the tip 1252 and the inner tube 1221 and outer tube 1222 are attached.

The deployment device 1200 further includes a mesh 1212. The mesh 1212 is configured to be compressed against the outer tube 1222 when the deployment device 1200 is inserted into a patient's vessel, and expand inside the vessel when released from the outer tube 1222. The mesh thus lines the interior of the vessel when it is released. In its compressed state, the mesh 1212 surrounds the outer tube 1222 and is removably coupled to the hub 114 and to the outer tube 1222. The mesh 1212 is operably coupled to the actuator 116.

The deployment device 1200 further includes a lock 1248. The lock 1248 is configured to hold the mesh 1212 in a compressed state against the outer tube 1222 in a locked position prior to engagement of the actuator 116. The lock 1248 is disposed on a portion of the tip 1252. The lock 1248 is positioned on the protrusion 1260 and compresses the mesh 1212 against the protrusion 1260 prior to engagement of the actuator 116. This configuration allows the deployment device 1200 to be compact in order to be inserted into the patient's vessel. Once the deployment device 1200 is inserted into the patient's vessel, the actuator 116 may be engaged.

In the illustrated embodiment, engagement of the actuator 116 about the y-axis causes translational motion of the mesh 1212 in the x-axis. For example, rotation of the actuator 116 causes the mesh 1212 to retract in a proximal direction along the central axis A. Retraction of the mesh 1212 releases the mesh 1212 from beneath the lock 1248. The mesh 1212 then expands in the vessel to line the interior of the vessel. In the illustrated embodiment, retraction of the mesh 1212 causes the lock 1248 to transition from the locked position on the protrusion 1260 to an unlocked position on the distal groove 1269. In alternative embodiments, the lock may stay in place on the protrusion 1260 when the mesh 1212 retracts.

Figure 13:
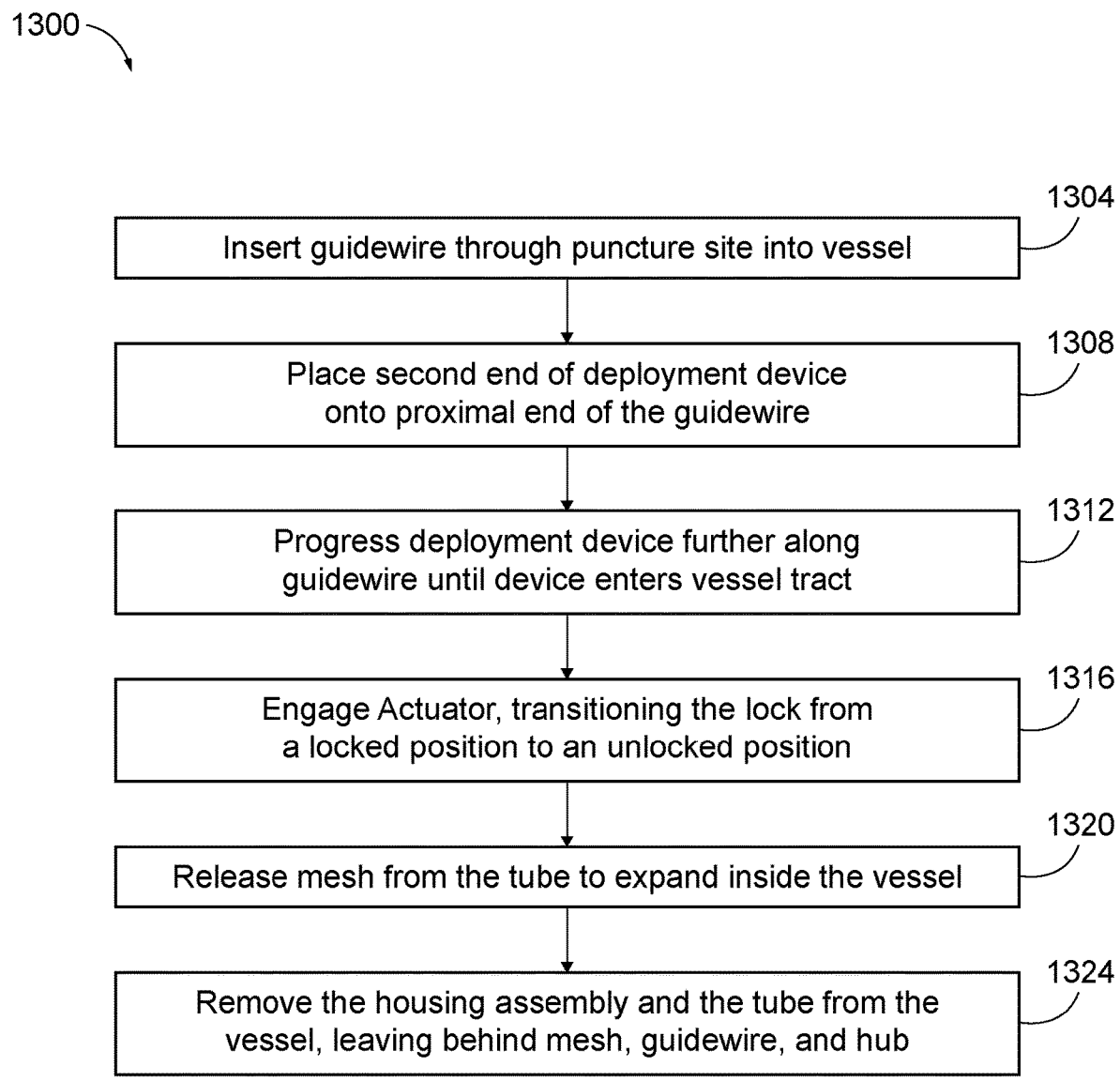
FIG. 13 is a process flow diagram illustrating a method for lining a vessel.

Now referring to FIG. 13, a method 1300 for lining a patient's vessel using the deployment device 100, 1100, 1200 shown in FIGS. 1-4, and 10A-12 will be described. In step 1304, a guidewire 106 is inserted through a puncture site 110 of a patient's vessel 102. The guidewire 106 passes through the puncture site 110 and protrudes into the vessel lumen. In step 1308, the second end 128 of the deployment device 100, 1100, 1200 is placed onto the proximal end of the guidewire 106 via the tip 152, 1252 and the deployment device 100, 1100, 1200 is slid along the guidewire 106. In step 1312, the deployment device 100, 1100, 1200 is progressed further along the guidewire 106 until a distal end of the deployment device 100, 1100, 1200 has entered the patient's vessel tract. The deployment device 100, 1100, 1200 is progressed along the guidewire 106 and into the patient's vessel tract until the hub 114 is in contact with the patient's skin. In step 1316, when the hub 114 is in contact with the patient's skin, the actuator 116 actuates at least one of the tube 120 and the mesh 112, 1112, 1212. In step 1320, the lock 148, 1148, 1248 releases the mesh 112, 1112, 1212 from the tube 120, 1222 such that the mesh 112, 1112, 1212 expands inside the vessel to line the interior of the vessel. In step 1324, the housing assembly 104 and the tube 120, 1221, 1222 of the deployment device 100, 1100, 1200 is removed from the vessel, leaving behind the mesh 112, 1112, 1212 and guidewire 106 inside the vessel, as well as the hub 114 in contact with the patient's skin 118. The remainder of the surgical procedure may then be completed before the mesh 112, 1112, 1212 the hub 114, and the guidewire 106 are removed, and the puncture site 110 is subsequently sealed.

The present disclosure is described herein using a limited number of embodiments, these specific embodiments are not intended to limit the scope of the disclosure as otherwise described and claimed herein. Modification and variations from the described embodiments exist. More specifically, the following examples are given as a specific illustration of embodiments of the claimed disclosure. It should be understood that the invention is not limited to the specific details set forth in the examples.

What is claimed:
1. A deployment device configured to line a vessel, the deployment device comprising:
   a housing having a proximal end and a distal end opposite the proximal end, the housing defining a guidewire channel that extends from the distal end of the housing toward the proximal end;
   a tube elongated along a longitudinal axis, the tube having a proximal end, a distal end spaced from the proximal end of the tube along the longitudinal axis, a protrusion, and a distal groove between the protrusion and the distal end of the tube; and
   a sheath assembly having:
      a hub removably coupled to the distal end of the housing such that the housing is removable from the sheath assembly; and
      a mesh removably coupled to the protrusion on the tube between the proximal end of the tube and the distal groove via a lock, the mesh being positioned along the tube;

wherein at least one of the tube and the mesh are movable along the longitudinal axis in order to de-couple the mesh from the tube; and wherein the lock engages with a proximal end of the protrusion such that the mesh expands and the lock engages with the distal groove such that the lock remains on the tube.

2. The deployment device of claim 1, wherein the lock is movable from a locked position, where the mesh is fixed to the tube, to an unlocked position where the mesh is not fixed to the tube.

3. The deployment device of claim 2, wherein the tube defines a proximal surface,
a distal stop surface spaced from the proximal surface along the longitudinal axis in a distal direction, and wherein the lock is disposed between the proximal surface and the distal stop surface.

4. The deployment device of claim 3, wherein a proximal groove is positioned between the proximal surface and the protrusion, and the distal groove is positioned between the protrusion and the distal stop surface, where the protrusion is positioned between and spaced from the proximal surface and the distal stop surface and wherein the lock is a) disposed on the protrusion to fix the mesh to the tube in the locked position, and b) is not disposed on the protrusion to release the mesh in the unlocked position.

5. The deployment device of claim 3, wherein the distal stop surface is configured to prevent the lock from advancing over the distal end of the tube along the distal direction.

6. The deployment device of claim 3, wherein the proximal surface is configured to inhibit movement of the lock in a proximal direction that is opposite the distal direction.

7. The deployment device of claim 1, wherein the lock is metallic.

8. The deployment device of claim 1, further comprising an actuator coupled to the tube and configured to move the tube from a first position to a second position that is distal to the first position.

9. The deployment device of claim 8, wherein the actuator is a lever configured to rotate about an actuator axis that is perpendicular to the longitudinal axis, wherein rotation of the lever about the actuator axis causes the tube to translate along the longitudinal axis.

10. The deployment device of claim 8, wherein the actuator includes a button coupled to a spring, the button configured to be depressed along the longitudinal axis to cause the tube to translate along the longitudinal axis.

11. The deployment device of claim 8, wherein the actuator is configured to rotate about the longitudinal axis to cause the tube to translate along the longitudinal axis.

12. The deployment device of claim 8, wherein the actuator is a pin configured to be displaced along a first axis to cause the tube to translate along a second axis that is perpendicular to the first axis.

13. The deployment device of claim 8, wherein the actuator is a tab coupled to a track having at least one ridge, the tab configured to be progressed on the track over the at least one ridge along the longitudinal axis to cause the tube to translate along the longitudinal axis.

14. The deployment device of claim 8, wherein the actuator is a gear coupled to a track, the gear configured to rotate about a first axis and cause the tube to translate along a second axis that is perpendicular to the first axis.

15. The deployment device of claim 1, wherein the tube is at least a 5 French sized tube.

16. A deployment device configured to line a vessel, the deployment device comprising:

a housing having a proximal end, a distal end opposite the proximal end, and a guidewire channel that extends from the proximal end to the distal end of the housing;
a tube extending relative to the housing in a distal direction, the tube having a protrusion, a proximal groove between a proximal end of the tube and the protrusion, and a distal groove between the protrusion and a distal end of the tube;
a sheath assembly having:
a hub removably coupled to the distal end of the housing; and
a mesh removably coupled to the tube, the mesh being positioned along the tube in a compressed state; and
a lock directly coupled to the protrusion on the tube between the proximal groove and the distal groove, and removably coupling the mesh to the protrusion of the tube, wherein the lock engages with the proximal groove and is configured to release the mesh from the protrusion of the tube such that the mesh expands, and wherein the lock engages with the distal groove such that the lock remains on the tube.

17. The deployment device of claim 16, wherein the lock is disposed on the distal end of the tube.

18. The deployment device of claim 17, wherein the lock is movable from a locked position, where the mesh is fixed to the tube, to an unlocked position where the mesh is not fixed to the tube.

19. The deployment device of claim 18, wherein the tube defines
a proximal surface configured to taper in a distal direction,
a distal stop surface spaced from the proximal surface along a longitudinal axis in a distal direction, and wherein the lock is disposed between the proximal surface and the distal stop surface.

20. The deployment device of claim 19, wherein the proximal groove is positioned between the proximal surface and the protrusion, and the distal groove is positioned between the protrusion and the distal stop surface, where the protrusion is positioned between and spaced from the proximal surface and the distal stop surface and wherein the lock is a) disposed on the protrusion to fix the mesh to the tube in the locked position, and b) is not disposed on the protrusion to release the mesh in the unlocked position.

21. The deployment device of claim 20, wherein the distal stop surface is configured to prevent the lock from advancing over the distal end of the tube along the distal direction.

22. The deployment device of claim 16, wherein the lock is metallic.

23. The deployment device of claim 16, further comprising an actuator coupled to the tube and configured to move the mesh from a first position to a second position that is distal to the first position.

24. The deployment device of claim 23, wherein the actuator is a lever configured to rotate about an actuator axis that is perpendicular to a longitudinal axis, wherein rotation of the lever about the actuator axis causes the mesh to translate along the longitudinal axis.

25. A deployment device configured to line a vessel, the deployment device comprising:
a housing having a proximal end, a distal end opposite the proximal end, and a guidewire channel that extends from the proximal end to the distal end of the housing;
an inner tube extending relative to the housing in a distal direction;
an outer tube extending relative to the housing in the distal direction and configured to surround the inner tube, the outer tube having a protrusion, a proximal groove between a proximal end of the outer tube and the protrusion, and a distal groove between the protrusion and a distal end of the outer tube;

a sheath assembly having:
- a hub removably coupled to the distal end of the housing; and
- a mesh removably coupled to the outer tube, the mesh being positioned along the outer tube in a compressed state and configured to release from the outer tube when moved; and a lock directly coupled to the protrusion on the outer tube that removably couples the mesh to the protrusion of the outer tube and is configured to transition from a locked position to an unlocked position where the lock engages with the proximal groove such that the mesh expands and where the lock engages with the distal groove such that the lock remains on the outer tube.

26. The deployment device of claim 25, further comprising a hollow tip configured to attach to the inner tube and the outer tube.

27. The deployment device of claim 26, wherein the hollow tip defines a distal stop surface spaced from a proximal surface along a longitudinal axis in a distal direction, and wherein the lock is disposed between the outer tube and the distal stop surface.

28. The deployment device of claim 27, further comprising the proximal groove between the outer tube and the protrusion, and the distal groove is positioned between the protrusion and the distal stop surface, wherein the protrusion is positioned between and spaced from the outer tube and the distal stop surface and wherein the lock is disposed on the protrusion to fix the mesh to the outer tube in the locked position, and is not disposed on the protrusion to release the mesh in the unlocked position.

29. The deployment device of claim 25, further comprising an actuator coupled to the outer tube and configured to move the mesh from a first position coupled to the lock to a second position that is distal to the first position and decoupled from the lock.

* * * * *